US00PP14581P29

(12) United States Plant Patent
Kataoka

(10) Patent No.: US PP14,581 P2
(45) Date of Patent: Mar. 9, 2004

(54) *GAURA LINDHEIMERI* PLANT NAMED 'CHERRY BRANDY'

(50) Latin Name: *Gaura lindheimeri*
Varietal Denomination: Cherry Brandy

(75) Inventor: Michio Kataoka, Niitsu (JP)

(73) Assignee: Nichien Co., Ltd., Niigata (JP)

( * ) Notice: Subject to any disclaimer, the term of this patent is extended or adjusted under 35 U.S.C. 154(b) by 0 days.

(21) Appl. No.: 10/287,384

(22) Filed: Nov. 4, 2002

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—Louanne Krawczewicz Myers
(74) *Attorney, Agent, or Firm*—Webb Ziesenheim Logsdon Orkin & Hanson, P.C.

(57) ABSTRACT

A new and distinct *Gaura lindheimeri* plant with red-purple colored flowers and a long blooming season.

3 Drawing Sheets

Botanical classification: *Gaura lindheimeri.*
Varietal denomination: 'Cherry Brandy'.

BACKGROUND OF THE INVENTION

The present invention comprises a new and distinct cultivar of *Gaura lindheimeri* known by the varietal name 'Cherry Brandy'. The new variety was discovered in Niigata, Japan. All trials and selections were conducted in Niigata, Japan. The new variety is the result of a planned breeding program between unpatented, unnamed *Gaura lindheimeri cerisier* (both parents). The new variety exhibits similar blooming time to both parents, but has a more compact habit and different height, leaf size, and flower color than both parents. The new variety exhibits similar flower color to the unpatented variety 'Siskyou Pink', but has uniform foliage with no spotting, a free branching habit, and a different height. The new variety was first asexually reproduced by vegetative terminal cuttings in Niigata, Japan. The new variety has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
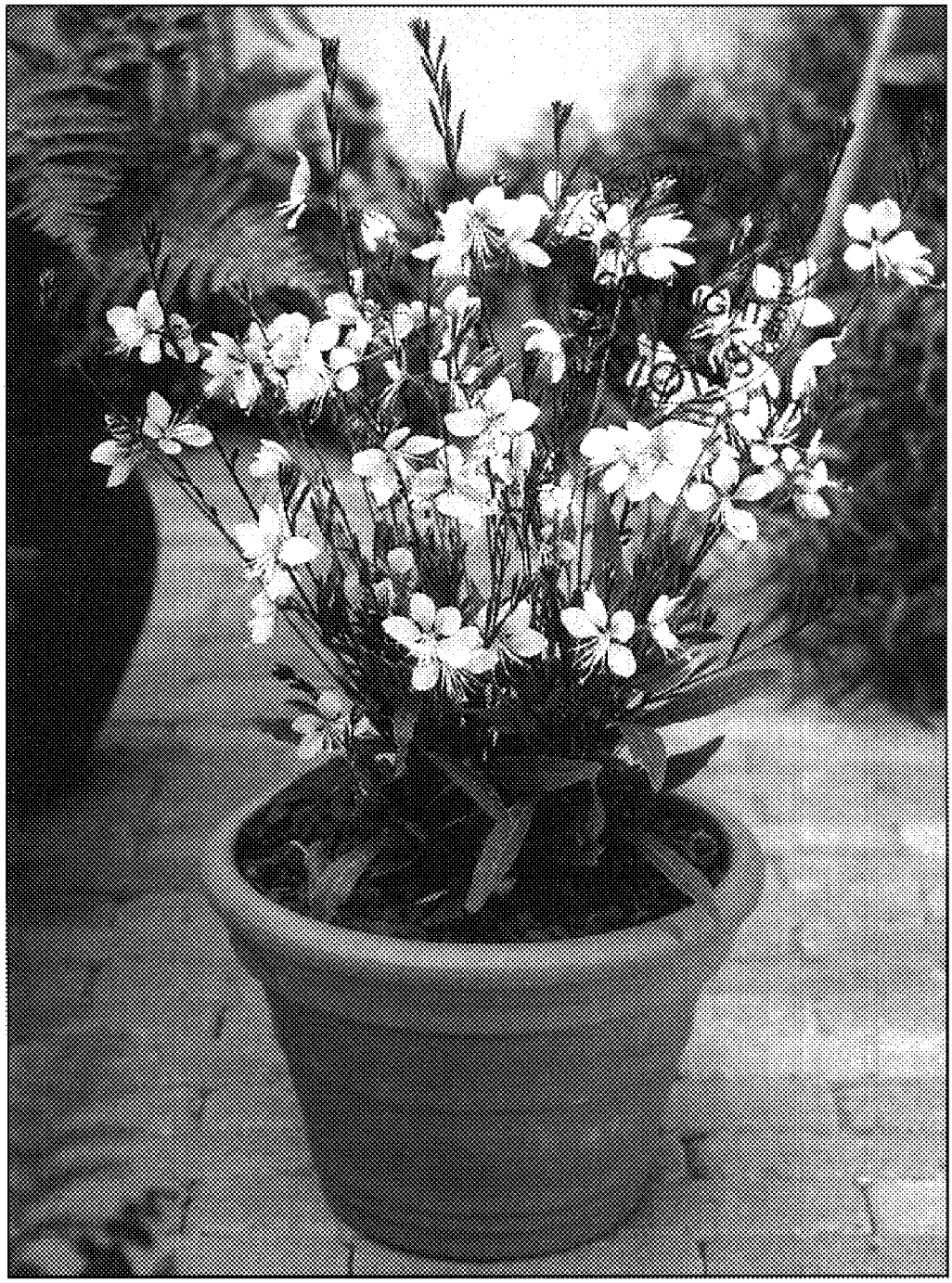
FIG. 1 is a photograph of the new plant.
Figure 2:
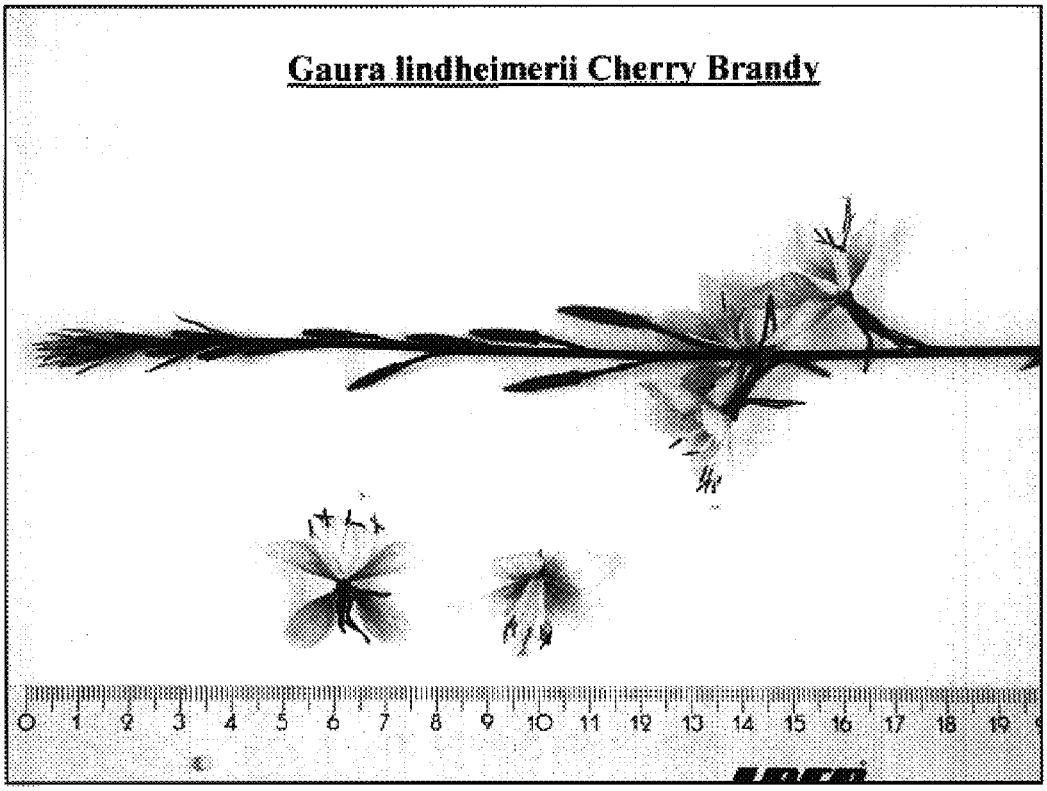
FIG. 2 is a photograph of the spike and flowers of the new plant.
Figure 3:
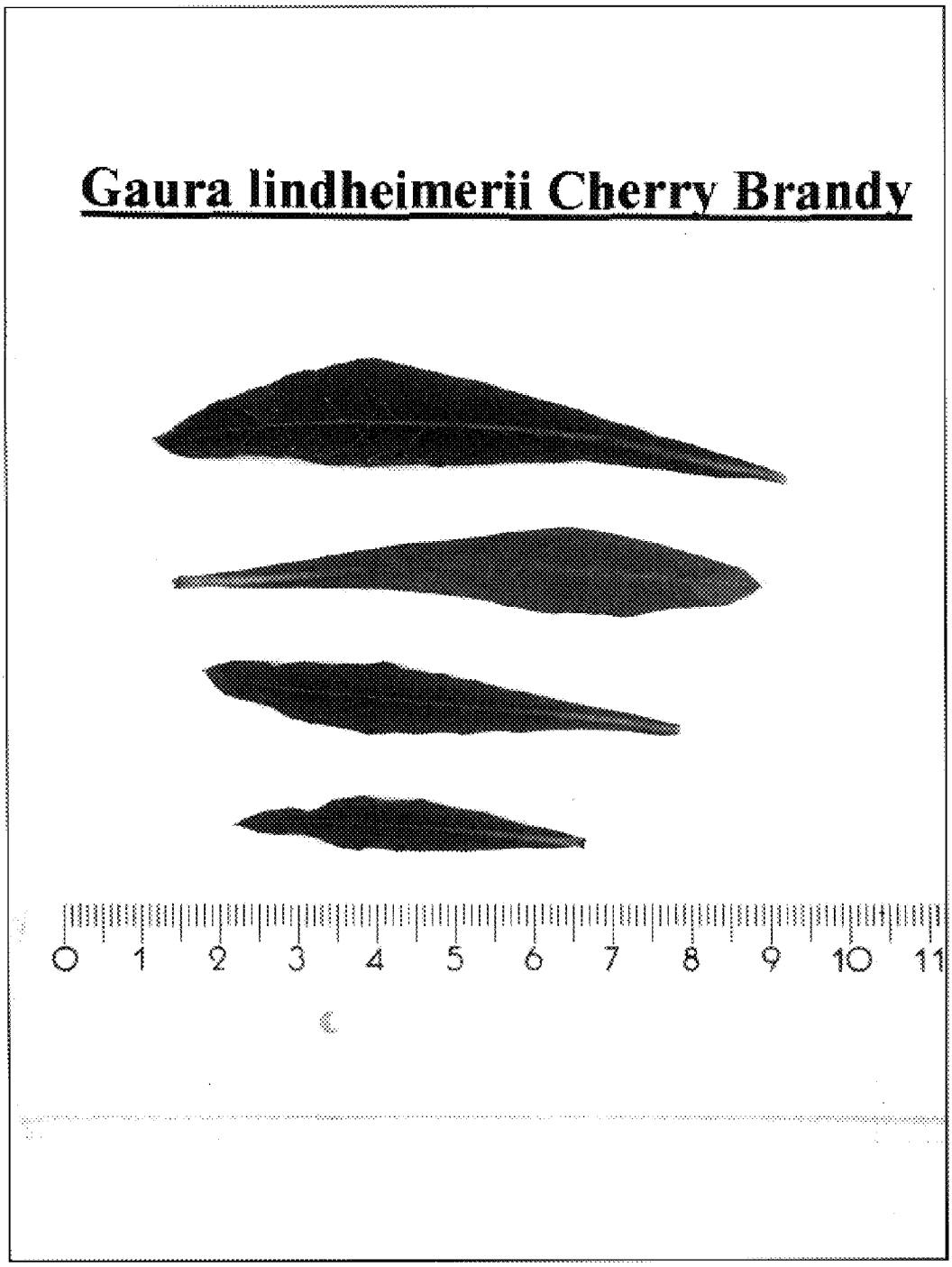
FIG. 3 is a photograph of the leaves of the new plant.

The following detailed description sets forth the characteristics of the new cultivar grown outside in the open ground and in 15 cm diameter containers with no extra fertilizer in The Netherlands. Plants were about 4 to 5 months old. The data which defines these characteristics were collected by asexual reproductions by cuttings. The color readings were taken in The Netherlands in natural daylight. Color references are primarily to The R.H.S. Colour Chart of The Royal Horticultural Society of London.

Plant:

*Time to initiate roots.*—About 10 days at 22° C.

*Time to develop roots.*—About 30 days at 18° C.

*Time to produce a finished flowering plant from a rooted cutting.*—About 6 weeks in a 9 cm container.

*Form.*—Upright.

*Stem.*—Length: 35–40 cm. Diameter: Average 4 mm. Color: 146C flushed with 59A. Texture: Smooth. Pubescence: Light. Form: Erect.

*Height.*—Blooms are 30 cm above soil when grown in a pot and 45 cm above soil when grown in the ground.

*Diameter.*—20 cm.

*Vigor.*—Medium.

*Branching habit.*—Free.

*Lateral branches.*—Length: 15–20 cm. Diameter: About 2 mm. Internode length: 2.0 cm average, but irregular. Texture: Smooth. Pubescence: Light. Color: 146A.

*Foliage.*—Arrangement: Alternate. Size of leaf: Length: 8.0 cm. Width: 1.2 cm. Shape of leaf: Oblanceolate. Shape of apex: Acute. Shape of base: Attenuate. Texture: Soft, slightly pubescent. Margin type: Entire, slightly undulate. Pubescence: On upper and lower surfaces.

*Color.*—Young leaves: Upper surface: Between 137A and 137B. Lower surface: Between 137B and 137C. Mature leaves: Upper surface: 137A. Lower surface: 137B.

*Petiole.*—None present.

*Veins.*—Color: Upper surface: 59B. Lower surface: 60C.

Flower:

*Bud.*—Stage when bud characteristics determined: Fully developed. Shape: Linear. Diameter: About 2 mm. Length: About 14 mm. Color: 60A.

*Natural flowering season.*—In Northern Europe from May to November outside.

*Spike.*—Number of flowers: Average 27. Length: Average 15 cm.

*Diameter across bloom.*—Average 4.0 cm.

*Corolla.*—Form: Zygomorphic. Petals/lobes: Number: 4. Length: About 16 mm. Width: About 8 mm.

Shape: Obovate. Apex: Rounded (obtuse). Base: Cuneate. Margin: Entire. Texture and appearance: Smooth, matte. Color (when opening and fully opened): Upper surface: Between 62D and 65D. Lower surface: Between 62D and 65D. Veins: Upper surface: Between 67B and 67C. Lower surface: Between 67B and 67C.

*Calyx.*—Form: Fused at tip. Length: About 15 mm. Diameter: About 2 mm. Sepal number: 4(2 joined pairs). Sepal shape: Linear. Sepal margin: Entire. Sepal texture: Smooth, pubescent. Sepal size: Length: About 15 mm. Width: About 2 mm. Sepal color: Upper surface: Between 59A and 59B. Lower surface: Between 59D and 60D. Pedicel: Length: 8 mm. Width: 1.5 mm. Color: 59A. Peduncle: Length: 15–20 cm. Width: 1.5 mm. Color: 137A shaded with 183A.

*Fragrance.*—None.

*Disease resistance.*—Good.

*Temperature tolerance.*—Good.

*Drought tolerance.*—Good.

*Lasting quality.*—Flowers last 1 day individually.

Reproductive organs:

*Stamens.*—Number: 8 per flower. Filament length: About 11 mm. Anthers: Shape: Linear. Length: 3.5 mm. Color: 59A. Pollen: Color: 3B. Amount: Plentiful.

*Pistils.*—Number: One. Length: 24 mm. Style: Length: 23 mm. Color: 155C flushed with 62A. Stigma: Shape: Four-ovals in cruciform. Color: 2D.

I claim:

1. A new and distinct variety of *Gaura lindheimeri* plant substantially as shown and described.

* * * * *